US012370139B2

(12) United States Patent
Van Der Geest et al.

(10) Patent No.: US 12,370,139 B2
(45) Date of Patent: **\*Jul. 29, 2025**

(54) USE OF EDARAVONE IN ORAL TREATMENT OF OXIDATIVE-STRESS MEDIATED NEURODEGENERATIVE DISORDERS

(71) Applicant: TREEWAY TW001 B.V., Rotterdam (NL)

(72) Inventors: Ronald Van Der Geest, Rotterdam (NL); Sytske Hyke Moolenaar, Rotterdam (NL)

(73) Assignee: TREEWAY TW001 B.V., Rotterdam (NL)

( \* ) Notice: Subject to any disclaimer, the term of this patent is extended or adjusted under 35 U.S.C. 154(b) by 388 days.

This patent is subject to a terminal disclaimer.

(21) Appl. No.: 16/733,958

(22) Filed: Jan. 3, 2020

(65) Prior Publication Data

US 2020/0138712 A1      May 7, 2020

Related U.S. Application Data

(63) Continuation of application No. PCT/EP2018/068396, filed on Jul. 6, 2018.

(30) Foreign Application Priority Data

Jul. 6, 2017  (EP) .................................. 17180087
Feb. 20, 2018 (EP) .................................. 18157678

(51) Int. Cl.
*A61K 9/08* (2006.01)
*A61K 9/00* (2006.01)
*A61K 9/14* (2006.01)
*A61K 31/4152* (2006.01)
*A61P 25/28* (2006.01)

(52) U.S. Cl.
CPC .............. *A61K 9/08* (2013.01); *A61K 9/0053* (2013.01); *A61K 9/14* (2013.01); *A61K 31/4152* (2013.01); *A61P 25/28* (2018.01)

(58) Field of Classification Search
CPC .......... A61K 9/08; A61K 9/0053; A61P 25/28
See application file for complete search history.

(56) References Cited

U.S. PATENT DOCUMENTS

| 2009/0076014 A1\* | 3/2009 | Oppenheimer ...... A61K 9/4808 514/249 |
| 2019/0083463 A1 | 3/2019 | Zhou et al. |

FOREIGN PATENT DOCUMENTS

| CN | 1449754 A | 10/2003 |
| CN | 100352520 C | 12/2007 |
| CN | 100358520 C \* | 1/2008 |
| CN | 101953832 A | 1/2011 |
| CN | 102349893 A | 2/2012 |
| CN | 103251554 | 8/2013 |
| CN | 105816423 | 8/2016 |
| EP | 1 405 637 A | 4/2004 |
| EP | 1 714 960 A | 10/2006 |
| EP | 2 754 440 A | 7/2014 |
| EP | 1714960 B1 \* | 3/2018 | ........... C07D 231/22 |
| JP | 2011032220 A \* | 2/2011 |
| WO | WO-2012/019381 | 2/2012 |
| WO | WO-2018/133957 A1 | 7/2018 |
| WO | WO-2018/134243 | 7/2018 |
| WO | WO-2019/008144 A1 | 1/2019 |

OTHER PUBLICATIONS

Jiao, PNAS, 112, 16, 2015 (Year: 2015).\*
Jiao, PNAS, Supporting information, 2015 (Year: 2015).\*
Cruz, Martin Paspe, "Edaravone (Radicava): A Novel Neuroprotective Agent for the Treatment of Amyotrophic Lateral Sclerosis", Drug Forecast, vol. 43, N. 1, Jan. 2018 (4 pages).
Hayashi et al., "Efficacy of Edaravone, a Free Radical Scavenger, on Left Ventricular Function and Structure in Diabetes Mellitus", Journal of Cardiovascular Pharmacology, vol. 41, No. 6, Jun. 2003 (7 pages).
International Preliminary Report on Patentability for PCT/EP2017/067005 dated May 9, 2019 (9 pages).
International Preliminary Report on Patentability for PCT/EP2018/051097 dated May 14, 2019 (14 pages).
International Search Report and Written Opinion of the International Searching Authority for PCT/EP2017/067005 dated Oct. 4, 2017 (11 pages).
International Search Report and Written Opinion of the International Searching Authority for PCT/EP2018/051097 dated Apr. 26, 2018 (12 pages).
Ishizawa et al., "An antioxidant treatment potentially protects myocardial energy metabolism by regulating uncoupling protein 2 expression in a chronic β-adrenergic stimulation rat model", Life Sciences, vol. 78, 2006 (9 pages).
Jiao et al., "Supporting Information" for Edaravone alleviates Alzheimer's disease-type pathologies and cognitive deficits, Proceedings National Academy of Sciences PNAS, Apr. 6, 2015 (10 pages).
Parikh et al., "Lipid-based nanosystem of edaravone: development, optimization, characterization and in vitro/in vivo evaluation", Drug Delivery, vol. 24, No. 1, 2017 (17 pages).
Rong et al., "Hydroxypropyl-sulfobutyl-β-cyclodextrin improves the oral bioavailability of edaravone by modulating drug efflux pump of enterocytes", Journal of Pharmaceutical Sciences, vol. 103, Issue 2, Feb. 2014 (13 pages).
Awad et al., "The history of 0.9% Saline" Clinical Nutrition, 2008, vol. 27, pp. 197-188 (10 pages).

(Continued)

*Primary Examiner* — Robert A Wax
*Assistant Examiner* — William Craigo
(74) *Attorney, Agent, or Firm* — Foley & Lardner LLP

(57) ABSTRACT

The present invention relates to the use of a liquid aqueous solution of edaravone in the treatment of an oxidative stress-mediated neurodegenerative disorder in a human patient, said treatment comprising at least once daily oral administration of the liquid edaravone solution to the human patient, to provide a daily dose of 40-120 mg edaravone during an uninterrupted period of at least 10 days. Examples of oxidative stress-mediated neurodegenerative disorders that can be treated in this way include amyotrophic lateral sclerosis (ALS), multiple sclerosis (MS), cerebral amyloid angiopathy (CAA), Alzheimer's disease and Parkinson's disease.

8 Claims, No Drawings

(56) References Cited

OTHER PUBLICATIONS

International Preliminary Report on Patentability issued in International Application No. PCT/EP2018/068396, mailed on Oct. 23, 2019.
International Search Report and Written Opinion issued in International Application No. PCT/EP2018/068396, mailed on Oct. 8, 2018.
Jiao, et al.; "Edaravone alleviates Alzheimer's disease-type pathologies and cognitive deficits"; Proceedings of the National Academy of Sciences of the United States of America, vol. 112, No. 16, pp. 5225-5230; Apr. 21, 2015 (XP055445120).
Mitsubishi Tanabe Pharma Corporation, "Radicut Injection 30 mg"; pp. 1-8; Jun. 1, 2015 (XP002777674); Retrieved from the Internet: http://www.e-search.ne.jp/~jpr/PDF/MT18.pdf [retrieved on Jan. 26, 2018].
Parikh, et al.; "Development of a novel oral delivery system of edaravone for enhancing bioavailability"; International Journal of Pharmaceutics; vol. 515, No. 1-2, pp. 490-500; Oct. 24, 2016 (XP002770642).
Sato, et al.; "A Novel Administration Route of Edaravone—II: Mucosal Absorption of Edaravone/Hydroxypropyl-Beta-Cyclodextrin Complex Solution Including L-Cysteine and Sodium Hydrogen Sulfite"; Pharmacology: International Journal of Experimental and Clinical Pharmacology; vol. 85, No. 2, pp. 88-94; Jan. 31, 2010 (XP009507098).
Zeng et al., "Preparation and physicochemical characteristics of the complex of edaravone with hydroxypropyl-β-cyclodextrin", Carbohydrate Polymers, 2011; pp. 1101-1105, vol. 82, No. 3, 2010 Elsevier Ltd.

\* cited by examiner

USE OF EDARAVONE IN ORAL TREATMENT OF OXIDATIVE-STRESS MEDIATED NEURODEGENERATIVE DISORDERS

CROSS-REFERENCE TO RELATED APPLICATIONS

The present application is a Continuation of International Patent Application No. PCT/EP2018068396, filed Jul. 6, 2018, and claims the benefit of priority to European Patent Application No. 18157678.6, filed Feb. 20, 2018, International Patent Application No. PCT/EP2018051097, filed Jan. 17, 2018, and European Patent Application No. 17180087.3, filed Jul. 6, 2017, the entire contents of which are hereby incorporated by reference.

TECHNICAL FIELD OF THE INVENTION

This invention relates to the use of 3-methyl-1-phenyl-2-pyrazolin-5-one (edaravone) in the treatment of an oxidative stress-mediated neurodegenerative disorder in human patients, said treatment comprising at least once daily oral administration of a liquid aqueous solution of edaravone. Examples of oxidative stress-mediated neurodegenerative disorders that can be treated in accordance with the present invention include amyotrophic lateral sclerosis (ALS), multiple sclerosis (MS), cerebral amyloid angiopathy (CAA), Alzheimer's disease and Parkinson's disease.

The invention further concerns a pharmaceutical kit comprising a plurality of oral dosage units, each dosage unit comprising either a liquid aqueous solution of edaravone or a particulate formulation containing edaravone.

BACKGROUND OF THE INVENTION

Oxidative stress arises from an alteration in the balance between the generation of reactive oxygen species (ROS) and their removal, together with the inability of the biological system to remove or repair damage that is caused by the effect of ROS on many cellular pathways. Oxidative stress can either be the cause or consequence of mitochondrial dysfunction as oxidative metabolism in mitochondria leads to the generation of ROS. Neurons are particularly vulnerable to redox dysregulation due to their large size and high oxygen consumption.

There is widespread recognition that ROS play key roles in normal brain function and pathology in the context of neurological disease. Oxidative stress is suspected to be important in neurodegenerative diseases including ALS, Alzheimer's disease, Parkinson's disease and MS. Indirect evidence via monitoring biomarkers such as reactive oxygen species, and reactive nitrogen species production, antioxidant defence indicates oxidative damage is involved in the pathogenesis of these diseases. Furthermore, cumulative oxidative stress with disrupted mitochondrial respiration and mitochondrial damage have been linked with the aforementioned neurodegenerative diseases.

ALS is a neurodegenerative disorder, which affects both the upper motor neurons, located in the brain, and the lower motor neurons, located in the spinal cord and brainstem. Upper motor neuron degeneration generally causes muscle spasticity, while lower motor neuron degeneration causes muscle weakness, muscle atrophy and twitching. Oxidative stress and mitochondrial dysfunction are both known pathophysiological mechanisms playing a role in ALS.

Early symptoms of ALS typically include muscle weakness in the hands, arms, legs or feet, causing weakness or spasticity in these body parts. The disease may also present itself in the muscles controlling speech or swallowing resulting in difficult chewing, speaking, swallowing, and breathing. As the disease progresses, it spreads to other parts of the body leading to progressive muscle weakness and paralysis. ALS patients ultimately lose their ability to initiate and control all voluntary movement and neuromuscular respiratory failure makes breathing increasingly difficult. Early symptoms and the development of the disease vary with each individual.

Sensory nerves and the autonomic nervous system remain unaffected, leaving hearing, sight, touch, smell, and taste intact as well as the involuntary muscles such as those that control heartbeat, gastrointestinal tract, bowel and bladder function. Cognitive function generally remains unaffected as well.

Most people who develop ALS are between the ages of 40 and 70, but the disease can also occur at a younger age. Prevalence has been found to increase with age. Although ALS is classified as a rare disease it is the most common motor neuron disease. About one or two out of 100,000 people develop ALS each year while the prevalence of ALS is estimated to be about two cases per 100,000 population, with increasing numbers due to the aging population.

Paspe Cruz (*Edaravone (Radicava) A Novel Neuroprotective Agent for the Treatment of Amyotrophic Lateral Sclerosis*, Drug Forecast, January (2018); 43(1), 25-28) reports that Riluzole, the first FDA-approved treatment for the disease, provides limited benefit to patients. More recently, edaravone, a potent pyrazolone free radical scavenger and antioxidant, was approved by the FDA for the treatment of ALS. Edaravone is available as a clear, colorless liquid provided as a sterile injection solution supplied for intravenous (IV) infusion in a polypropylene bag containing 30 mg edaravone in 100 mL of isotonic solution. The recommended dose of edaravone is 60 mg administered via 60-minute IV infusion once daily for 14 days as the initial treatment cycle, followed by a 14-day drug-free period. Subsequent treatment cycles consist of once-daily dosing for 10 days out of 14 day-periods, each followed by a 14-day drug-free period.

Alzheimer's disease (AD) is a chronic neurodegenerative disease that usually starts slowly and worsens over time. It is the cause of 60% to 70% of cases of dementia. Oxidative stress participates in the development of Alzheimer's disease by promoting $A\beta$ deposition, tau hyperphosphorylation, and the subsequent loss of synapses and neurons. Jiao et al. (*Edaravone alleviates Alzheimer's disease-type pathologies and cognitive deficits*, Proc Natl Acad Sci USA, Apr. 21 (2015); 112(16), 5225-5230) describe a study in which edaravone was administered to APP/PS1 mice. Edaravone prominently attenuated the cognitive deficits, as reflected by reduced escaping latency in platform testing and increased annulus crossing during the probing test. Oral intake of edaravone also to markedly alleviated $A\beta$ plaque burden in the hippocampus and neocortex. The $A\beta$ levels in the brain were also significantly reduced by the oral intake.

Parkinson disease (PD) is a chronic, progressive neurological disease that is associated with the preferential loss of dopaminergic neurons in the substantia nigra pars compacta (SNc) of the brain, lower levels of dopamine in the corpus stratum and the appearance of intraneuronal inclusions, termed Lewy bodies and neurites, containing $\alpha$ synuclein aggregates. The exact etiology of the disease still remains elusive, but mitochondrial dysfunction, neuroinflammation and environmental factors are increasingly appreciated as key determinants of dopaminergic neuronal susceptibility in PD, in both familial and sporadic forms of the disease. In both cases, oxidative stress is thought to be the common underlying mechanism that leads to cellular dysfunction and eventual cell death.

There is growing awareness that disease progression in multiple sclerosis (MS) is not only associated with an autoimmune degradation of myelin but also with axonal degeneration, and accumulating data indicate that oxidative stress plays a major role in the pathogenesis of MS. Increased levels of biomarkers of oxidative stress and/or decreased levels of uric acid, a natural scavenger of peroxynitrite are seen in blood and CSF of MS patients. ROS and RNS generated by macrophages have been implicated as mediators of demyelination and axonal injury in both experimental autoimmune encephalomyelitis (EAE, the generally accepted animal model for the study of MS) and MS.

Cerebral amyloid angiopathy (CAA) is a common disorder caused by the deposition of Aβ in the vessel wall of small arterial vessels of the brain, leading to cerebral hemorrhage, ischemia, and infarction. Reactive oxygen species are a key contributor to CAA formation, CAA-induced vessel dysfunction, and CAA-related microhemorrhage.

Oral administration of edaravone in different forms has been investigated in in vivo animal studies.

Hayashi et al. (*Efficacy of Edaravone, a Free Radical Scavenger, on Left Ventricular Function and Structure in Diabetes Mellitus*, J Cardiovasc Pharmacol., June (2003); 41(6), 923-929) describe a study in which edaravone was orally administered at 10, 30, and 100 mg/kg to male Wistar rats, and the plasma concentration were measured (243 ng/mL, 1314 ng/mL and 10999 ng/mL, respectively).

Sato et al. (*A Novel Administration Route of Edaravone-II: Mucosal Absorption of Edaravone from Edaravone/Hydroxypropyl-Beta-Cyclodextrin Complex Solution Including L-Cysteine and Sodium Hydrogen Sulfite*, Pharmacology (2010); 85, 88-94) examined the pharmacokinetics of edaravone when edaravonehydroxypropyl-β-cyclodextrin (HPβCD) complex solution, including L-cysteine (L-Cys) and sodium hydrogen sulfite (SHS), was administered intravenously, rectally and via the oral mucosa of Wistar rats. bioavailability of oral mucosal, rectal and oral administration was about 100, 63.5 and 26.6%, respectively.

CN 101 953 832 describes an oral pharmaceutical composition comprising cyclodextrin in combination with edaravone. The examples of the Chinese patent application describe tablets, capsules and granules containing cyclodextrin-edaravone complex. The examples further describe a bioavailability study that was conducted in SD rats. Results show that in comparison to intravenous administration, oral bioavailabilty of non-complexed edaravone was appr. 5.8%, whereas oral bioavailability of the cyclodextrin-edaravone complexes tested was in the range of 56-65%.

Rong et al. (*Hydroxypropyl-Sulfobutyl-β-Cyclodextrin Improves the Oral Bioavailability of Edaravone by Modulating Drug Efflux Pump of Enterocytes*, Journal of Pharmaceutical Sciences (2013), DOI 10.1002/jps.23807, 1-13) describe a study in which the effect of hydroxypropyl-sulfobutyl-β-cyclodextrin on the bioavailability and intestinal absorption of edaravone was investigated. It was found that the inclusion complex of edaravone-cyclodextrin improved the water solubility of edaravone and enhanced the bioavailability of bioavailability of edaravone in rats. Table 2 of this article shows that at a dose of 27 mg/kg the absolute bioavailability ($F_{abs}$) of orally administered 'raw' edaravone (suspended with 0.5% CMC-Na) was only 5.23% (compared to 100% bioavailability of intravenously administered edaravone). Table 2 further shows that oral bioavailability could be improved by more than factor 10 by complexing edaravone with cyclodextrin.

Jiao et al.(*Edaravone alleviates Alzheimer's disease-type pathologies and cognitive deficits*, Proc Natl Acad Sci USA, Apr. 21 (2015); 112(16), 5225-5230) describe a study in which edaravone was orally administered to APP/PS1 Mice at 33.2 mg/kg/d between the ages of 3 and 12 mo. Based on the pharmacokinetic result, the bioavailability of oral edaravone was 38% of the i.v. delivery.

Parikh et al. (*Development of a novel oral delivery system of edaravone for enhancing bioavailability*, International Journal of Pharmaceutics, (2016); 515, 490-500) discuss the development of an oral delivery system of edaravone. The authors describe a Novel Oral Delivery System of edaravone (NODS) that is made up of a mixture of Labrasol and an acidic aqueous system that was optimized on the basis of a solubility and stability study. The NODS delivery system contained 30 mg/mL of edaravone. The in-vivo oral bioavailability of the NODS delivery system was investigated in adult rats using a dose of 30 mg edaravone per kg bodyweight. It was found that the oral bioavailability of the NODS delivery system was 5.7 times higher than that of an edaravone suspension containing 30 mg/mL edaravone and 0.5% sodium carboxymethyl cellulose (see Table 2).

Parikh et al. (*Lipid-based nanosystem of edaravone: development, optimization, characterization and in vitro/in vivo evaluation*, Drug Delivery, (2017); 24(1), 962-978) describe a study that aimed at enabling oral use of edaravone by developing a lipid-based nanosystem (LNS). The components of LNS including oil, surfactants, and co-surfactants were selected based on their potential to maximize the solubilization in gastrointestinal (GI) fluids, reduce its glucuronidation and improve transmembrane permeability. A liquid LNS (L-LNS) in the form of a micro-emulsion was prepared, comprising Capryol™ PGMC (Oil), Cremophor0 RH 40:Labrasol® :TPGS 1000 (1:0.8:0.2) (Surfactant) and Transcutol® P (Co-surfactant). It was found that (at 30 mg/kg bodyweight) the oral bioavailability of the L-LNS was almost 11 times higher than that of an edaravone suspension containing 30 mg/mL edaravone and 0.5% sodium carboxymethyl cellulose (Table 3).

SUMMARY OF THE INVENTION

It was unexpectedly discovered that the known treatment of oxidative stress-mediated neurodegenerative disorders by intravenous infusion of edaravone can be replaced by at least once daily oral administration of a liquid edaravone solution to provide a daily dose of 40-120 mg edaravone. The oral dose of edaravone used in the treatment according to the present invention is of the same order of magnitude as the intravenous dose of 60 mg edaravone per day that is recommended for treatment of ALS.

It was found that oral bioavailability of aqueous edaravone solutions in humans is unexpectedly high and that, following oral administration of the aqueous edaravone solution, edaravone is absorbed at a surprisingly fast rate. Unexpectedly, the inventors have discovered that orally administered edaravone is metabolised in essentially the same way as intravenously administered edaravone. In both cases the bulk of the edaravone is metabolised to sulfate and glucuronide conjugates, and also the ratio in which sulfate and glucuronide conjugates are formed is very similar.

The oral treatment of ALS and other oxidative stress-mediated neurodegenerative disorders with edaravone in accordance with the present invention offers several advantages. First of all, unlike the known intravenous treatment, it does not require administration by a medical practitioner. Secondly, the present treatment does not require planning of drug-free periods. Finally, patients generally prefer oral administration over intravenous administration.

The present invention also provides a pharmaceutical kit comprising a plurality of oral dosage units, each dosage unit comprising a sealed container holding 20-150 ml of a liquid aqueous edaravone solution, wherein the total amount of edaravone contained in the liquid edaravone solution within each dosage unit is in the range of 40-120 mg.

Further provided is a pharmaceutical kit comprising a plurality of oral dosage units, each dosage unit comprising 0.5-6 g of a particulate edaravone formulation, wherein the total amount of edaravone contained in the particulate edaravone formulation within each dosage unit is in the range of 40-120 mg, more preferably in the range of 60-110 mg and most preferably in the range of 70-100 mg.

DETAILED DESCRIPTION OF THE INVENTION

Accordingly, the present invention relates to a liquid aqueous solution of edaravone for use in the treatment of an oxidative stress-mediated neurodegenerative disorder in a human patient, said treatment comprising at least once daily oral administration of the liquid edaravone solution to the human patient, to provide a daily dose of 40-120 mg edaravone during an uninterrupted period of at least 10 days.

The term "edaravone" as used herein refers to the substance 3-methyl-1-phenyl-2-pyrazolin-5-one, including pharmaceutically acceptable salts thereof.

The daily dose of edaravone as mentioned herein refers to the amount of edaravone equivalent. The term "edaravone equivalent" as used herein refers to the quantity of edaravone (3-methyl-1-phenyl-2-pyrazolin-5-one) that is contained in a given quantity of edaravone salt.

The term "oxidative stress-mediated neurodegenerative disorder" as used herein refers to a neurodegenerative disorder that is as at least partially mediated by oxidative stress. In other words, the neurodegenerative disorder may additionally be mediated by one or more other mediators besides oxidative stress.

The term "treatment" as used herein encompasses both therapeutic and palliative treatment.

The treatment according to the present invention may contain one or more holiday periods during which no edaravone is administered. Preferably, the liquid edaravone solution is at least once daily administered to provide the daily dose of 40-120 mg edaravone during an uninterrupted period of at least 4 week, more preferably of at least 8 weeks, even more preferably of at least 12 weeks.

The liquid edaravone solution is preferably orally administered to treat an oxidative stress-mediated neurodegenerative disorder selected from amyotrophic lateral sclerosis (ALS), multiple sclerosis (MS), cerebral amyloid angiopathy (CAA), Alzheimer's disease and Parkinson's disease. The present treatment is particularly suitable for the treatment of ALS, Alzheimer's disease and Parkinson's disease, and most particularly for the treatment of ALS. According to a particularly preferred embodiment, the liquid edaravone solution of the present invention does not contain any undissolved edaravone.

The treatment of ALS in accordance with the present invention preferably comprises once daily of twice daily administration of the liquid edaravone solution. Most preferably, the treatment comprises once daily administration of the liquid edaravone solution.

The liquid edaravone solution is preferably orally administered to the human patient in an amount providing 0.5-2.5 mg edaravone per kg of bodyweight per day. Even more preferably, the liquid edaravone solution is administered in an amount providing 0.8-2.2 mg edaravone per kg of bodyweight per day, most preferably in an amount providing 1.0-2.0 mg edaravone per kg of bodyweight per day.

Edaravone is preferably present in the liquid edaravone solution in a concentration of 0.5-3 mg/mL, more preferably of 0.8-2.5 mg/mL, most preferably of 1-2.5 mg/mL.

Preferably, the liquid edaravone solution is orally administered to the human patient in an amount of 30-150 mL. More preferably, the liquid edaravone solution is orally administered in an amount of 40-120 mL, most preferably in an amount of 50-110 mL.

In the present treatment, the liquid edaravone solution is preferably orally administered in an amount providing 60-110 mg edaravone per day, most preferably 70-100 mg edaravone per day.

The liquid edaravone solution typically contains at least 85 wt. % water. More preferably, the liquid edaravone solution contains at least 90 wt. % water, most preferably at least 95 wt. % water.

According to a particularly preferred embodiment, the present treatment of ALS slows the advance of the disease.

In another preferred embodiment of the present treatment the human patient has fasted for at least 1 hour before oral administration of the liquid edaravone solution.

According to a particularly preferred embodiment of the present invention, the liquid edaravone solution that is orally administered to the human patient is prepared within 3 hours prior to oral administration by mixing a particulate edaravone formulation comprising edaravone with aqueous liquid, preferably by mixing the dry particulate edaravone formulation with water.

The aforementioned particulate edaravone formulation preferably comprises an alkalizing agent, more preferably an alkalizing agent is selected from oxides and hydroxides of alkaline metals; oxides and hydroxides of alkali-earth metals; $Al(OH)_3$; $Fe_2O_3$; salts of weak organic and weak inorganic acids, alkaline amines; alkaline amino acids; and combinations thereof. The oxides and hydroxides of alkaline metals are preferably selected from NaOH, KOH, LiOH and combinations thereof. The oxides and hydroxides of alkali-earth metals are preferably selected from $Ca(OH)_2$, CaO, $Mg(OH)_2$, MgO and combinations thereof. The salts of weak organic and weak inorganic acids are preferably selected from carbonate, bicarbonate, borate, carboxylate (e.g. lactate, citrate, acetate, formate and oxalate), phosphate, sulfate and combinations thereof. The alkaline amines are preferably selected from tris(hydroxymethyl)aminomethane, ethanolamine, diethanolamine, triethanolamine, N-methyl-glucamine, glucosamine, ethylenediamine, diethylamine, triethylamine, isopropylamine, diisopropylamine, ammonia and combinations thereof. The alkaline amino acids are preferably selected from arginine, histidine, lysine and combinations thereof. It was found that the rate at which edaravone dissolves in water is increased substantially in the presence of an alkalizing agent, especially when dosed in aqueous liquid at concentrations equivalent to at least 0.3 grams edaravone per liter.

The particulate edaravone formulation, when added to demineralized water of 25° C. in a concentration equivalent to an edaravone concentration of 1.4 g/l, preferably produces a solution having a pH that is at least 0.5 pH units, more preferably at least 1 pH unit higher than the pH of a solution having the same edaravone concentration and consisting exclusively of edaravone and demineralized water.

The liquid edaravone solution that is prepared by mixing the particulate edaravone formulation with aqueous liquid preferably has a pH in the range of 6.0 to 9.0, more preferably in the range of 6.5 to 8.8, more preferably in the range of 6.8 to 8.5. Besides edaravone and water, the liquid edaravone solution may contain one or more further components. Examples of such additional components include anti-oxidants, pH-regulators, preservatives and sodium chloride.

The liquid edaravone solution of the present invention preferably does not contain edaravone-cyclodextrin inclusion complex.

Another aspect of the invention relates to a pharmaceutical kit comprising a plurality of oral dosage units, each dosage unit comprising a sealed container holding 20-150 ml of a liquid aqueous edaravone solution, wherein the total amount of edaravone contained in the liquid edaravone solution within each dosage unit is in the range of 40-120 mg, more preferably in the range of 60-110 mg and most preferably in the range of 70-100 mg.

Preferably, the liquid aqueous edaravone solution in the oral dosage unit is a liquid edaravone solution as defined herein before.

The present kit preferably comprises at least 5, more preferably least 10 and most preferably at least 14 of the oral dosage units comprising liquid edaravone solution.

The sealed containers in the present kit preferably each hold 25-50 ml of the liquid edaravone solution.

The liquid edaravone solution in the sealed containers preferably is non-isotonic. Typically, the liquid edaravone solution in the sealed containers has an osmolarity of less than 250 mOsmL, more preferably of less than 180 mOsmL.

According to a particularly preferred embodiment, the kit comprises written instructions to once daily orally administer the liquid edaravone solution, optionally after dilution with aqueous liquid, to human patients suffering from ALS.

Yet another aspect of the invention relates to a pharmaceutical kit comprising a plurality of oral dosage units, each dosage unit comprising 0.5-6 g, preferably 0.8-5 g, more preferably 1-4 g of a particulate edaravone formulation, wherein the total amount of edaravone contained in the particulate edaravone formulation within each dosage unit is in the range of 40-120 mg, more preferably in the range of 60-110 mg and most preferably in the range of 70-100 mg.

The present kit preferably comprises at least 7, more preferably least 14 and most preferably at least 28 of the oral dosage units comprising the particulate edaravone formulation.

The particulate edaravone formulation preferably contains 15-200 mg/g, more preferably 20-150 mg/g of edaravone.

According to a particularly preferred embodiment, the kit comprises written instructions to once daily orally administer the particulate edaravone formulation, after dissolution in aqueous liquid, to human patients suffering from ALS.

The invention is further illustrated by the following non-limiting examples.

EXAMPLES

Example 1

A single dose, randomized, two-period, cross-over study was conducted in 18 healthy male and female human subjects.

The subjects received:

140 mg edaravone (p.o) in the form of 100 mL of a freshly prepared solution containing 1.5 grams of the dry formulation shown in Table 1

60 mg edaravone (i.v. 60 minutes), using two Radicut® ampoules (30 mg edaravone in 20 mL solution)

TABLE 1

|  | wt. % |
|---|---|
| Edaravone (micronized) | 9.3 |
| Mannitol | 56.8 |
| Sodium orthophosphate | 33.3 |
| Sodium lauryl sulfate | 0.5 |
| Total | 100.0 |

Blood samples were taken just before and at regular intervals after administration, and the edaravone plasma concentration of each sample was determined. The averaged results of these measurements are shown in Table 2. Parameters indicative of the relative bioavailability are presented in Table 3.

TABLE 2

| | Edaravone plasma concentration (ng/ml) | |
|---|---|---|
| Time (hrs) | oral administration (140 mg) | i.v. infusion (60 mg) |
| Pre | 0 | 0 |
| 0.083 | 1197 | n.d. |
| 0.17 | 2358 | 380 |
| 0.25 | 2627 | n.d. |
| 0.5 | 1806 | 713 |
| 1 | 689 | 990 |
| 1.5 | 354 | 321 |
| 2 | 203 | n.d. |
| 4 | 68 | 42 |
| 6 | 24 | 14 |
| 8 | 13 | 8 |
| 10 | 9 | 5 | n.d.: not determined

TABLE 3

| | oral administration | i.v. infusion |
|---|---|---|
| $T_{max}$ (hr) | 0.25 | 1 |
| $C_{max}$ (ng/ml) | 2936 | 1030 |
| $AUC_{last}$ (h · ng/ml) [1] | 2389 | 1292 |
| $AUC_{0-inf}$ (h · ng/ml) [2] | 2413 | 1304 |

[1] $AUC_{last}$ is the area under the plasma concentration-time curve from time of administration until the last measurable plasma concentration
[2] $AUC_{0-inf}$ is the area under the plasma concentration-time curve from time of administration until (extrapolated) infinity These results demonstrate that orally administered edaravone exhibits rapid absorption with peak maximum concentrations reached at about 15 min after administration and shows good systemic bioavailability ($F_{abs}$=79%) compared to i.v. infusion.

Example 2

The study described in Example 1 was repeated, again using 18 healthy male and female human subjects. This time, besides overall edaravone plasma concentration, also the concentrations non-metabolised edaravone and of two edaravone metabolites (edaravone sulfate conjugate and edaravone glucuronide conjugate) were determined.

The averaged results of these measurements are shown in Tables 4, 5 and 6.

TABLE 4

| | Edaravone plasma concentration (ng/ml) | |
|---|---|---|
| Time (hrs) | oral administration (140 mg) | i.v. infusion (60 mg) |
| Pre | 0 | 0 |
| 0.083 | 1530 | n.d. |
| 0.17 | 2761 | 373 |
| 0.25 | 3060 | n.d. |
| 0.5 | 2003 | 696 |
| 1 | 762 | 943 |
| 1.5 | 388 | 298 |
| 2 | 228 | n.d. |
| 4 | 63 | 36 |
| 6 | 24 | 13 |
| 8 | 13 | 7 |
| 10 | 8 | 5 | n.d.: not determined

TABLE 5

| | oral administration | i.v. infusion |
|---|---|---|
| $T_{max}$ (hr) | 0.23 | 1 |
| $C_{max}$ (ng/ml) | 3531 | 943 |
| $AUC_{last}$ (h · ng/ml) [1] | 2564 | 1216 |
| $AUC_{0-inf}$ (h · ng/ml) [2] | 2569 | 1211 |

[1] $AUC_{last}$ is the area under the plasma concentration-time curve from time of administration until the last measurable plasma concentration
[2] $AUC_{0-inf}$ is the area under the plasma concentration-time curve from time of administration until (extrapolated) infinity

TABLE 6

| | Ratio conjugate-to-parent drug $(AUC_{last})$[1] | |
|---|---|---|
| | oral administration (n = 18) | i.v. infusion (n = 18) |
| Non-conjugated | 1 | 1 |
| Sulfate conjugate | 9.5 ± 2.8 | 9.9 ± 2.7 |
| Glucuronide conjugate | 1.8 ± 0.8 | 1.4 ± 1.0 |

[1]Ratio is calculated using $AUC_{last}$ (h · μMol/L)

These results demonstrate that orally administered edaravone exhibits rapid absorption with peak maximum concentrations reached at about 14 min after administration and shows good systemic bioavailability ($F_{abs}$=93%) compared to i.v. infusion.

No indication for a relevant contribution of gastrointestinal metabolism to the overall plasma metabolism profile of edaravone was found, since no increase in the relative contribution of (one of) the conjugates was observed shortly after oral administration (in comparison to intravenous administration). Furthermore, the ratio of sulfate and glucuronide conjugate-to-parent drug was similar after intravenous and oral administration.

The invention claimed is:

1. A method of treating an oxidative stress-mediated neurodegenerative disorder in a human patient, the treatment comprising orally administering at least once daily at least 30 mL of a liquid aqueous solution comprising at least 85 wt. % water and 0.5-3 mg/mL edaravone to the human patient to provide a daily dose of 40-120 mg edaravone during an uninterrupted period of at least 10 days, wherein the liquid edaravone solution does not contain an edaravone-cyclodextrin inclusion complex.

2. The method according to claim 1, wherein the liquid aqueous solution is administered to provide 0.5-2.5 mg edaravone per kg of bodyweight per day.

3. The method according to claim 1, wherein the liquid aqueous solution comprises 0.8-2.5 mg/mL edaravone.

4. The method according to claim 1, wherein the liquid aqueous solution is administered in an amount of 30-150 mL.

5. The method according to claim 1, wherein the liquid aqueous solution is administered to provide 60-100 mg edaravone per day.

6. The method according to claim 1, wherein the liquid aqueous solution is administered once daily or twice daily.

7. The method according to claim 1, wherein oxidative stress-mediated neurodegenerative disorder is selected from the group consisting of amyotrophic lateral sclerosis (ALS), multiple sclerosis (MS), cerebral amyloid angiopathy (CAA), Alzheimer's disease and Parkinson's disease.

8. The method according to claim 1, further comprising preparing the liquid aqueous solution by mixing a dry particulate edaravone formulation comprising edaravone with aqueous liquid.

* * * * *